United States Patent
Dzikowski

(10) Patent No.: US 9,629,364 B2
(45) Date of Patent: Apr. 25, 2017

(54) SYNERGISTIC WEED CONTROL FROM APPLICATIONS OF AMINOPYRALID AND CLOPYRALID

(71) Applicant: Dow AgroSciences LLC, Indianapolis, IN (US)

(72) Inventor: Marcin Dzikowski, Munich (DE)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/102,818

(22) Filed: Dec. 11, 2013

(65) Prior Publication Data

US 2014/0171322 A1 Jun. 19, 2014

Related U.S. Application Data

(60) Provisional application No. 61/737,413, filed on Dec. 14, 2012.

(51) Int. Cl.
*A01N 43/40* (2006.01)

(52) U.S. Cl.
CPC .................................. *A01N 43/40* (2013.01)

(58) Field of Classification Search
CPC ...................................................... A01N 43/40
USPC ......................................................... 504/130
See application file for complete search history.

(56) References Cited

U.S. PATENT DOCUMENTS

| | | | |
|---|---|---|---|
| 6,297,197 B1 | 10/2001 | Fields et al. | |
| 7,314,849 B2 | 1/2008 | Balko et al. | |
| 7,432,227 B2 | 10/2008 | Balko et al. | |
| 7,538,214 B2 | 5/2009 | Epp et al. | |
| 7,786,044 B2 | 8/2010 | Epp et al. | |
| 7,820,883 B2 | 10/2010 | Walsh et al. | |
| 7,863,220 B2 | 1/2011 | Clark et al. | |
| 8,203,033 B2 | 6/2012 | McCutchen et al. | |
| 8,309,491 B2 | 11/2012 | Li et al. | |
| 2006/0183637 A1 | 8/2006 | Loughner et al. | |
| 2007/0010399 A1 | 1/2007 | Rosinger et al. | |
| 2007/0021303 A1 | 1/2007 | Rosinger et al. | |
| 2007/0117721 A1 | 5/2007 | Keeney et al. | |
| 2008/0153704 A1 | 6/2008 | Yamaji et al. | |
| 2008/0242546 A1 | 10/2008 | Schultz et al. | |
| 2009/0011936 A1 | 1/2009 | Hawkes et al. | |
| 2009/0187021 A1 | 7/2009 | Youngman et al. | |
| 2010/0016158 A1 | 1/2010 | Kilian et al. | |
| 2010/0048399 A1 | 2/2010 | Hacker et al. | |
| 2010/0069248 A1 | 3/2010 | Hacker et al. | |
| 2010/0105558 A1 | 4/2010 | Li et al. | |
| 2010/0190794 A1 | 7/2010 | Hupe et al. | |
| 2010/0273656 A1 | 10/2010 | Sedun et al. | |
| 2010/0279862 A1 | 11/2010 | Bickers et al. | |
| 2010/0279864 A1 | 11/2010 | Mann et al. | |
| 2010/0285959 A1 | 11/2010 | Armel et al. | |
| 2010/0304973 A1 | 12/2010 | Rosinger et al. | |
| 2010/0311794 A1 | 12/2010 | Venkataramani | |
| 2011/0009264 A1 | 1/2011 | Hacker et al. | |
| 2011/0092367 A1 | 4/2011 | Griveau et al. | |
| 2011/0118120 A1 | 5/2011 | Corr et al. | |
| 2011/0136667 A1 | 6/2011 | Turner et al. | |
| 2011/0183845 A1 | 7/2011 | Loughner et al. | |
| 2011/0190130 A1 | 8/2011 | Carranza Garzon | |
| 2011/0190134 A1 | 8/2011 | Jousseaume et al. | |
| 2011/0190135 A1 | 8/2011 | Mann et al. | |
| 2011/0190136 A1 | 8/2011 | Hufnagl et al. | |
| 2011/0230349 A1 | 9/2011 | Buttimor | |
| 2011/0251070 A1 | 10/2011 | Poffenberger et al. | |
| 2011/0287932 A1 | 11/2011 | Hacker et al. | |
| 2011/0287935 A1 | 11/2011 | Patzoldt et al. | |
| 2011/0294663 A1 | 12/2011 | Hacker et al. | |
| 2012/0015808 A1 | 1/2012 | Rodriguez Contreras et al. | |
| 2012/0026909 A1 | 2/2012 | Seok | |
| 2012/0053053 A1 | 3/2012 | Boussemghoune et al. | |
| 2012/0058899 A1 | 3/2012 | Jensen et al. | |
| 2012/0071320 A1 | 3/2012 | Atkinson et al. | |
| 2012/0115816 A1 | 5/2012 | Ramsay et al. | |
| 2012/0142532 A1 | 6/2012 | Wright et al. | |
| 2012/0149572 A1 | 6/2012 | Gewehr et al. | |

(Continued)

FOREIGN PATENT DOCUMENTS

| | | |
|---|---|---|
| WO | 02/13942 | 2/2002 |
| WO | 2007027863 | 9/2007 |

(Continued)

OTHER PUBLICATIONS

Sendero label, Dow AgroSciences, Feb. 29, 2012.*
IP 88909D (Mar. 4, 2005).*
Picloram product safety assessment, Dow Chemical Co., Sep. 12, 2009.*
Norsworthy, J.K. et al., "Tolerance of leafy greens to preemergence and postemergence herbicides," Weed Technology, vol. 19(3), pp. 724-730 (2005).*
Goodall, J.M. et al., "The effects of five herbicides on Pinus patula saplings when applied 'over-the-top' for woody weed control," South African Forestry Journal, No. 157, Jun. 1991, pp. 38-45.*
Dow AgroSciences, "Mesquite Control with Sendero™ Brochure," (2012), 8 pages.
Dow AgroSciences, "Sendero™ Range & Pasture Herbicide," www.dowagro.com/range/products/sendero.htm (viewed Aug. 27, 2012), 2 pages.

(Continued)

*Primary Examiner* — John Pak
(74) *Attorney, Agent, or Firm* — Michael R. Asam; Meunier Carlin & Curfman, LLC

(57) ABSTRACT

Disclosed herein are herbicidal compositions comprising a synergistically herbicidal effective amount of (a) aminopyralid, or an agriculturally acceptable salt or ester thereof, and (b) clopyralid, or an agriculturally acceptable salt or ester thereof. Also disclosed herein are methods of controlling undesirable vegetation, which comprise applying to vegetation or an area adjacent the vegetation or applying to soil or water to prevent the emergence or growth of vegetation (a) aminopyralid, or an agriculturally acceptable salt or ester thereof, and (b) clopyralid, or an agriculturally acceptable salt or ester thereof, wherein (a) and (b) are each added in an amount sufficient to produce a synergistic herbicidal effect.

4 Claims, No Drawings

(56) References Cited

U.S. PATENT DOCUMENTS

| | | |
|---|---|---|
| 2012/0238449 A1 | 9/2012 | Mann |
| 2012/0284812 A1 | 11/2012 | Mankin et al. |
| 2013/0023413 A1 | 1/2013 | Hacker et al. |
| 2014/0031214 A1 | 1/2014 | Yerkes et al. |

FOREIGN PATENT DOCUMENTS

| | | |
|---|---|---|
| WO | 2008108973 | 9/2008 |
| WO | 2008121200 | 10/2008 |
| WO | 2009103451 | 8/2009 |
| WO | 2009153246 A2 | 12/2009 |
| WO | 2009153247 | 12/2009 |
| WO | 2009153247 A2 | 12/2009 |
| WO | 2010009819 | 1/2010 |
| WO | 2010017921 | 2/2010 |
| WO | 2010019377 | 2/2010 |
| WO | 2010046422 | 4/2010 |
| WO | 2010086437 | 8/2010 |
| WO | 2010149732 | 12/2010 |
| WO | 2011019652 | 2/2011 |
| WO | 2011097187 | 8/2011 |
| WO | 2011113052 | 9/2011 |
| WO | 2011/133482 | 10/2011 |
| WO | 2011/160162 | 12/2011 |
| WO | 2012009489 A2 | 1/2012 |
| WO | 2012018885 A1 | 2/2012 |
| WO | 2012037425 | 3/2012 |
| WO | 2012150333 | 11/2012 |
| WO | 2013026811 | 2/2013 |

OTHER PUBLICATIONS

Dow AgroSciences, "Using Sendero™ in Mesquite Treatment Methods Brochure," (2012), 26 pages.
International Search Report and Written Opinion, mailed Feb. 28, 2013, in related International Application No. PCT/US2012/069797.
Tomlin, C. D. S., Ed., The Pesticide Manual: A World Compendium, "Aminopyralid," 15th ed., BCPC: Alton, 2009, pp. 34-35.
Tomlin, C. D. S., Ed., The Pesticide Manual: A World Compendium, "Clopyralid," 15th ed., BCPC: Alton, 2009, pp. 224-226.
U.S. Appl. No. 13/715,230, filed Dec. 14, 2012, and the prosecution history thereof.
International Search Report and Written Opinion issued Feb. 28, 2013, in related International Patent Application No. PCT/US2012/69797.
Office Action issued in related U.S. Appl. No. 13/715,230 on Apr. 7, 2016.
Hart. New herbicide now available for Mesquite in Texas. Texas AM Cooperative agrilife extension. (Nov. 6, 2012) http://agrilife.org/agwest/2012/06/11/new-senderotm-herbicide-now-available-for-mesquite-control-in-texas/.
Cummings et al., "GF-2791, a new herbicide containing aminopyralid and clopyralid for honey mesquite (*Prosopis glandulosa*) control in southwestern rangelands," Presentation at the 65th Annual Meeting of the Society of Range Management, Spokane WA (Feb. 1, 2012).
Tran, H. et al. "Assessment of herbicides for selectively controlling broom (*Cystisus scoparius*) growing with Pinus radiata" 17th Australasian Weeds Conference, New Zealand Plant Protection Society, Sep. 26-30, 2010; p. 372.
"Aminopyralid: A New Herbicide," An IP.Com Prior Art Database Technical Disclosure (2005).
Cummings et al., "GF-2791, a new herbicide containing aminopyralid and clopyralid for honey mesquite (*Prosopis glandulosa*) control in southwestern rangelands," Abstracts of the 65th Annual Meeting of the Society of Range Management, 2012, Spokane WA, published Dec. 4, 2011, Abstract 0322.
Farm Chemical International, Crop Protection Database, "Aminopyralid," available at http://www.farmchemicalsinternational.com/crop-protection-database/#/product/detail/424163/ (accessed on Mar. 27, 2014).
Farm Chemical International, Crop Protection Database, "Clopyralid," available at http://www.farmchemicalsinternational.com/crop-protection-database/#/product/detail/100820/ (accessed on Mar. 28, 2014).
Bovey, R et al. "Herbicide mixtures for control of honey mesquite (*Prosopis glandulosa*)," HCAPLUS 1985:418304 (abstract).
Ledbetter, "AgriLife Extension Helps Test New Mesquite Control Herbicide," AgriLife Today (Jun. 19, 2012), 3 pages.
International Search Report and Written Opinion issued Mar. 19, 2014, in related International Patent Application No. PCT/US2013/070247.
International Search Report and Written Opinion issued Feb. 28, 2014, in related International Patent Application No. PCT/US2012/69797.
Transline Label, Dow AgroSciences, Jul. 26, 1999.
Milestone Label, DowAgroSciences, Aug. 29, 2005.
Cummings et al., "GF-2791, a new herbicide containing aminopyralid and clopyralid for honey mesquite (*Prosopis glandulosa*) control in southwestern rangelands," Abstracts of the 65th Annual Meeting of the Society of Range Management, Spokane WA, Abstract 0322 (Dec. 15, 2011).
Green et al., "Effect of Aminopyralid and Clopyralid on Native Fortis and Grasses," Abstracts of the 65th Annual Meeting of the Society of Range Management, Spokane WA, Abstract 0227 (Dec. 15, 2011).
Third-Party Observations filed Sep. 12, 2014, in related International Patent Application No. PCT/US2012/069797.
Tran et al., Assessment of Herbicides for Selectively Controlling Broom (*Cytisus scoparius*) Growing with Pinus radiata, Seventeenth Austrasian Weeds Conference (2010).
Wallace et al., Effects of Aminopyralid on Ponderosa Pine (*Pinus ponderosa*), 5 Invasive Plant Sci. & Mgmt. 164-69 (2012).

* cited by examiner

SYNERGISTIC WEED CONTROL FROM APPLICATIONS OF AMINOPYRALID AND CLOPYRALID

CROSS REFERENCE TO RELATED APPLICATIONS

This application claims the benefit of priority to U.S. Provisional Patent Application No. 61/737,413 filed Dec. 14, 2012, the disclosure of which is expressly incorporated herein by reference.

FIELD OF THE DISCLOSURE

The present disclosure relates to herbicidal compositions comprising a synergistically herbicidal effective amount of (a) aminopyralid or an agriculturally acceptable salt or ester thereof, and (b) clopyralid or an agriculturally acceptable salt or ester thereof. The present disclosure also relates to methods for controlling undesirable vegetation.

BACKGROUND

Many recurring problems in agriculture involve controlling growth of undesirable vegetation that can, for instance, inhibit crop growth. To help control undesirable vegetation, researchers have produced a variety of chemicals and chemical formulations effective in controlling such unwanted growth. However, a continuing need exists for new compositions and methods to control growth of undesirable vegetation.

SUMMARY OF THE DISCLOSURE

Herbicides of many types have been disclosed in the literature and a number are in commercial use. In some cases, herbicidal active ingredients have been found more effective in combination than when applied individually and this is referred to as "synergy" or "synergism." The present disclosure is based on the discovery that (a) aminopyralid, or an agriculturally acceptable salt or ester thereof, and (b) clopyralid, or an agriculturally acceptable salt or ester thereof, display a synergistic herbicidal effect when applied in combination.

Accordingly, the present disclosure relates to herbicidal compositions comprising a synergistically herbicidal effective amount of (a) aminopyralid, or an agriculturally acceptable salt or ester thereof, and (b) clopyralid, or an agriculturally acceptable salt or ester thereof. In some embodiments, (a) includes the potassium salt of aminopyralid. In some embodiments, (b) includes clopyralid-olamine. In some embodiments, the herbicidal composition is for crop use. The acid equivalent weight ratio of (a) to (b) can be less than 1:2. In some embodiments, the acid equivalent weight ratio of (a) to (b) is 1:600 to 1:6 (e.g., from 1:150 to 1:30). In some embodiments, the composition further comprises an additional pesticide (e.g., aminocyclopyrachlor, amicarbazone, 4-aminopicolinic acids, bromoxynil, chlorsulfuron, 2,4-D, dicamba, dichlorprop-P, diclosulam, diuron, florasulam, flucarbazone-sodium, flumetsulam, fluoroxypyr, glyphosate, glufosinate, imazamox, imazapyr, imazapic, imazaquin, imazethapyr, imazamethabenz, indaziflam, ioxynil, MCPA, mecoprop-P, metsulfuron-methyl, oxyfluorfen, penoxsulam, picloram, pinoxaden, pyroxsulam, rimsulfuron, sulfometuron, thifensulfuron-methyl, tebuthiuron, tribenuron-methyl, triclopyr, or agriculturally acceptable salts or esters or mixtures thereof). The additional pesticide can include 2,4-D choline salt, triclopyr choline salt, or a mixture thereof. In some embodiments, the composition is free of naptalam and salts and esters thereof. In some embodiments, the composition further comprises a herbicidal safener, an agriculturally acceptable adjuvant or carrier, or a combination thereof.

The present disclosure also relates to methods of controlling undesirable vegetation, which comprise applying to vegetation or an area adjacent the vegetation or applying to soil or water to prevent the emergence or growth of vegetation (a) aminopyralid, or an agriculturally acceptable salt or ester thereof and (b) clopyralid, or an agriculturally acceptable salt or ester thereof, wherein (a) and (b) are each added in an amount sufficient to produce a synergistic herbicidal effect. In some embodiments, (a) and (b) are applied simultaneously. In some embodiments, (a) and (b) are applied postemergence to the undesirable vegetation. The undesirable vegetation can be controlled in, for instance, barley, canola, cereal, corn, mint, mustard seed, oats, spinach, sugar beet, turnips, or wheat. In some embodiments, the undesirable vegetation is a broadleaf weed (e.g., nightshade). The undesirable vegetation can be controlled in crops tolerant to glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, bromoxynil, or combinations thereof. For example, the undesired vegetation can be controlled in phenoxy acid tolerant crops and the phenoxy acid tolerant crops have tolerance conferred by an AAD12 gene. In some embodiments, the undesirable vegetation is resistant to auxinic herbicides. In some embodiments, (a) is applied in an amount of from 0.1-10 grams of acid equivalent per hectare (g ae/ha) (e.g., 0.5-3 g ae/ha). In some embodiments, (b) is applied in an amount of from 20-300 g ae/ha (e.g., from 60-90 g ae/ha).

The description below sets forth details of one or more embodiments of the present disclosure. Other features, objects, and advantages will be apparent from the description and from the claims.

DETAILED DESCRIPTION

The present disclosure relates to herbicidal compositions comprising a synergistically herbicidal effective amount of (a) aminopyralid, or an agriculturally acceptable salt or ester thereof, and (b) clopyralid, or an agriculturally acceptable salt or ester thereof. The present disclosure also relates to methods for controlling undesirable vegetation.

The term "herbicide," as used herein, means an active ingredient that kills, controls, or otherwise adversely modifies the growth of vegetation. A "herbicidally effective amount" is an amount of an active ingredient that causes a "herbicidal effect," i.e., an adversely modifying effect that includes deviations from, for instance, natural development, killing, regulation, desiccation, and retardation. The terms "plants" and "vegetation" can include, for instance, germinant seeds, emerging seedlings, and established vegetation.

Aminopyralid

Compositions and methods of the present disclosure can include aminopyralid or an agriculturally acceptable salt or ester thereof. Aminopyralid (i.e., 4-amino-3,6-dichloro-2-pyridinecarboxylic acid), shown below, is a herbicide that can be used to control broadleaf weeds in, for instance, industrial vegetation, rangeland, and pastures. Its herbicidal activity is described in THE PESTICIDE MANUAL, Fifteenth Edition, 2009.

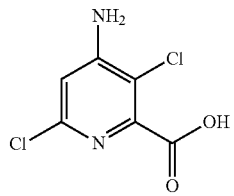 [SMILES: Nc1cc(Cl)nc(C(=O)O)c1Cl]

Aminopyralid can be provided in its acid form (as shown above), or as an agriculturally acceptable salt or ester thereof. Exemplary agriculturally acceptable salts or esters of aminopyralid include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium (e.g., triisopropanolammonium), mono-, di- and tri-hydroxy-C2-C8-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl) ammonium salts, their diglycolamine salts and their esters, in particular its $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, 2-ethylhexyl and butoxyethyl esters. Exemplary agriculturally acceptable salts or esters of aminopyralid can include aminopyralid-potassium, aminopyralid-olamine, aminopyralid-tris(2-hydroxypropyl) ammonium, aminopyralid-methyl, aminopyralid choline salt, and mixtures thereof. In some embodiments, the aminopyralid is provided as an amine salt, such as aminopyralid-olamine salt, dimethylamine (DMA) salt, monoethanolamine (MEA) salt, triisopropanolamine (TIPA) salt, or a mixture thereof. Aminopyralid and agriculturally acceptable salts or esters thereof are or have been commercially available, for example, under the trademark MILESTONE® (by Dow AGROSCIENCES LLC).

The aminopyralid or an agriculturally acceptable salt or ester thereof described herein can be used in an amount sufficient to induce a herbicidal effect. In some embodiments, the aminopyralid or agriculturally acceptable salt or ester thereof is applied to vegetation or an area adjacent the vegetation or applied to soil or water to prevent the emergence or growth of vegetation in an amount of 0.1 grams of acid equivalent per hectare (g ae/ha) or greater (e.g., 0.2 g ae/ha or greater, 0.3 g ae/ha or greater, 0.4 g ae/ha or greater, 0.5 g ae/ha or greater, 0.6 g ae/ha or greater, 0.7 g ae/ha or greater, 0.8 g ae/ha or greater, 0.9 g ae/ha or greater, 1 g ae/ha or greater, 1.2 g ae/ha or greater, 1.4 g ae/ha or greater, 1.6 g ae/ha or greater, 1.8 g ae/ha or greater, 2 g ae/ha or greater, 2.2 g ae/ha or greater, 2.4 g ae/ha or greater, 2.6 g ae/ha or greater, 2.8 g ae/ha or greater, 3 g ae/ha or greater, 3.5 g ae/ha or greater, 4 g ae/ha or greater, 4.5 g ae/ha or greater, 5 g ae/ha or greater, 5.5 g ae/ha or greater, 6 g ae/ha or greater, 6.5 g ae/ha or greater, 7 g ae/ha or greater, 7.5 g ae/ha or greater, 8 g ae/ha or greater, 8.5 g ae/ha or greater, 9 g ae/ha or greater, or 9.5 g ae/ha or greater). In some embodiments, the aminopyralid or agriculturally acceptable salt or ester thereof is applied to vegetation or an area adjacent the vegetation or applied to soil or water to prevent the emergence or growth of vegetation in an amount of 10 g ae/ha or less (e.g., 9.5 g ae/ha or less, 9 g ae/ha or less, 8.5 g ae/ha or less, 8 g ae/ha or less, 7.5 g ae/ha or less, 7 g ae/ha or less, 6.5 g ae/ha or less, 6 g ae/ha or less, 5.5 g ae/ha or less, 5 g ae/ha or less, 4.5 g ae/ha or less, 4 g ae/ha or less, 3.5 g ae/ha or less, 3.3 g ae/ha or less, 3.1 g ae/ha or less, 2.9 g ae/ha or less, 2.7 g ae/ha or less, 2.5 g ae/ha or less, 2.3 g ae/ha or less, 2.1 g ae/ha or less, 1.9 g ae/ha or less, 1.7 g ae/ha or less, 1.5 g ae/ha or less, 1.3 g ae/ha or less, 1.1 g ae/ha or less, 0.9 g ae/ha or less, 0.7 g ae/ha or less. 0.5 g ae/ha or less, or 0.3 g ae/ha or less). In some embodiments, the aminopyralid or agriculturally acceptable salt or ester thereof is applied to vegetation or an area adjacent the vegetation or applied to soil or water to prevent the emergence or growth of vegetation in an amount of from 0.1-10 g ae/ha (e.g., from 0.2-8 g ae/ha, from 0.25-7 g ae/ha, from 0.3-6 g ae/ha, from 0.35-5 g ae/ha, from 0.4-4 g ae/ha, from 0.5-3 g ae/ha, from 0.6-2.5 g ae/ha, 0.7-2.0 g ae/ha, 0.8-1.5 g ae/ha, 0.9-1.1 g ae/ha).

Clopyralid

Compositions and methods of the present disclosure can include clopyralid or an agriculturally acceptable salt or ester thereof. Clopyralid (i.e., 3,6-dichloropicolinic acid; 3,6-dichloro-2-pyridinecarboxylic acid), shown below, is a herbicide that can be used to control broadleaf weeds in, for instance, cereal crops, ornamentals, pastures, fallow, turf, rangelands, forest, and industrial applications. Its herbicidal activity is described in The Pesticide Manual, Fifteenth Edition, 2009.

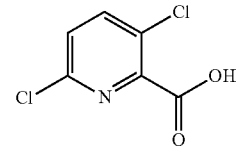 [SMILES: O=C(O)c1nc(Cl)ccc1Cl]

Clopyralid can be provided in its acid form (as shown above), or as an agriculturally acceptable salt or ester thereof. Exemplary agriculturally acceptable salts or esters of clopyralid include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-C2-C8-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, their diglycolamine salts and their esters, in particular its $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, 2-ethylhexyl and butoxyethyl esters; and aryl esters such as benzyl. Exemplary agriculturally acceptable salts or esters of clopyralid can include clopyralid-potassium, clopyralid-olamine, clopyralid-tris(2-hydroxypropyl) ammonium, clopyralid-methyl, and mixtures thereof. In some embodiments, the clopyralid is provided as an amine salt, such as clopyralid-olamine salt, dimethylamine (DMA) salt, monoethanolamine (MEA) salt, triisopropanolamine (TIPA) salt, or a mixture thereof. Clopyralid and agriculturally acceptable salts or esters thereof are or have been commercially available, for example, under the trademarks LONTREL® (by Dow AGROSCIENCES LLC), RECLAIM® (by Dow AGROSCIENCES LLC), DOW SHIELD® (by Dow AGROSCIENCES LLC), STINGER® (by Dow AGROSCIENCES LLC), TRANSLINE® (by Dow AGROSCIENCES LLC), FETREL® (by FERTIAGRO PTE. LTD.), CLEAN SLATE® (by NUFARM Americas Inc.), GARRISON® (by Nufarm Americas Inc.), PHAETON® (by Hektas Ticaret T.A.S.), CLOPYR® (by United Phosphorus Ltd.), CLEO® (by Parijat), WOPROCLOPYRALID® (by B.V. Industrie-& Handelsondernem-ing Simonis), BOSS® (by Stockton Agrimor AG), PIRATE® (by Willowood Ltd.), TRELAN® (by Willowood Ltd.), and TANGO® (by Zelam Ltd.).

The clopyralid or an agriculturally acceptable salt or ester thereof described herein can be used in an amount sufficient to induce a herbicidal effect. In some embodiments, the clopyralid or agriculturally acceptable salt or ester thereof is applied to vegetation or an area adjacent the vegetation or applied to soil or water to prevent the emergence or growth of vegetation in an amount of 20 grams of acid equivalent per hectare (g ae/ha) or greater (e.g., 30 g ae/ha or greater, 40 g ae/ha or greater, 50 g ae/ha or greater, 60 g ae/ha or greater, 70 g ae/ha or greater, 80 g ae/ha or greater, 90 g ae/ha or greater, 100 g ae/ha or greater, 110 g ae/ha or greater, 120 g ae/ha or greater, 130 g ae/ha or greater, 140 g ae/ha or greater, 160 g ae/ha or greater, 180 g ae/ha or greater, 200 g ae/ha or greater, or 250 g ae/ha or greater). In some embodiments, the clopyralid or agriculturally acceptable salt or ester thereof is applied to vegetation or an area adjacent the vegetation or applied to soil or water to prevent the emergence or growth of vegetation in an amount of 300 g ae/ha or less (e.g., 290 g ae/ha or less, 280 g ae/ha or less, 270 g ae/ha or less, 260 g ae/ha or less, 250 g ae/ha or less, 240 g ae/ha or less, 230 g ae/ha or less, 220 g ae/ha or less, 210 g ae/ha or less, 200 g ae/ha or less, 190 g ae/ha or less, 180 g ae/ha or less, 170 g ae/ha or less, 160 g ae/ha or less, 150 g ae/ha or less, 140 g ae/ha or less, 130 g ae/ha or less, 120 g ae/ha or less, 110 g ae/ha or less, 100 g ae/ha or less, 90 g ae/ha or less, 80 g ae/ha or less, 70 g ae/ha or less, 60 g ae/ha or less, 50 g ae/ha or less, 40 g ae/ha or less, or 30 g ae/ha or less). In some embodiments, the clopyralid or agriculturally acceptable salt or ester thereof is applied to vegetation or an area adjacent the vegetation or applied to soil or water to prevent the emergence or growth of vegetation in an amount of from 20-300 g ae/ha (e.g., from 25-250 g ae/ha, from 30-200 g ae/ha, from 35-180 g ae/ha, from 40-150 g ae/ha, from 50-120 g ae/ha, from 55-100 g ae/ha, or 60-90 g ae/ha).

Herbicidal Mixtures or Combinations

The (a) aminopyralid or an agriculturally acceptable salt or ester thereof is mixed with or applied in combination with (b) clopyralid or an agriculturally acceptable salt or ester thereof in an amount sufficient to induce a synergistic herbicidal effect. In some embodiments, (a) and (b) are used in an amount sufficient to induce a synergistic herbicidal effect while still showing good crop compatibility (i.e., their use in crops does not result in increased damage to crops when compared to the individual application of the herbicidal compounds (a) or (b)). As described in the *Herbicide Handbook* of the Weed Science Society of America, Ninth Edition, 2007, p. 429, "'synergism' [is] an interaction of two or more factors such that the effect when combined is greater than the predicted effect based on the response to each factor applied separately." Synergistic in the herbicide context can mean that the use of (a) and (b) as defined above results in an increased weed control effect compared to the weed control effects that are possible with the use of (a) or (b) alone. In some embodiments, the damage or injury to the undesired vegetation caused by the compositions and methods disclosed herein is evaluated using a scale from 0% to 100%, when compared with the untreated control vegetation, wherein 0% indicates no damage to the undesired vegetation and 100% indicates complete destruction of the undesired vegetation. In some embodiments, Colby's formula is applied to determine whether using (a) and (b) in combination shows a synergistic effect: S. R. Colby, *Calculating Synergistic and Antagonistic Responses of Herbicide Combinations*, Weeds 15, p. 22 (1967)

$$E = X + Y - \frac{X*Y}{100}$$

wherein

X=effect in percent using (a) aminopyralid or an agriculturally acceptable salt or ester thereof at an application rate a;

Y=effect in percent using (b) clopyralid or an agriculturally acceptable salt or ester thereof at an application rate b;

E=expected effect in percent (%) of (a)+(b) at application rates a and b.

In Colby's equation, the value E corresponds to the effect (plant damage or injury) that is to be expected if the activity of the individual compounds is additive. If the observed effect is higher than the value E calculated according to the Colby equation, then a synergistic effect is present according to the Colby equation.

In some embodiments, the compositions and methods disclosed herein are synergistic as defined by the Colby equation. In some embodiments, the joint action of aminopyralid or an agriculturally acceptable salt or ester thereof and clopyralid or an agriculturally acceptable salt or ester thereof results in enhanced activity against undesired vegetation (via synergism), even at application rates below those typically used for the pesticide to have a herbicidal effect on its own. In some embodiments, the compositions and methods disclosed herein can, based on the individual components, be used at lower application rates to achieve a herbicidal effect comparable to the effect produced by the individual components at normal application rates. In some embodiments, the compositions and methods disclosed herein provide an accelerated action on undesired vegetation (i.e., they effect damaging of undesired vegetation more quickly compared with application of the individual herbicides).

In some embodiments, the acid equivalent weight ratio of (a) aminopyralid or agriculturally acceptable salt or ester thereof to (b) clopyralid or an agriculturally acceptable salt or ester thereof that is sufficient to induce a synergistic herbicidal effect is at least 1:600 (e.g., at least 1:550, at least 1:500, at least 1:450, at least 1:400, at least 1:350, at least 1:300, at least 1:250, at least 1:200, at least 1:150, at least 1:140, at least 1:130, at least 1:120, at least 1:110, at least 1:100, at least 1:90, at least 1:80, at least 1:70, at least 1:60, at least 1:50, at least 1:40, at least 1:30, at least 1:25, at least 1:20, at least 1:15, at least 1:12, at least 1:10, at least 1:9, at least 1:8, or at least 1:7). In some embodiments, the acid equivalent weight ratio of (a) to (b) that is sufficient to induce a synergistic herbicidal effect is less than 1:2 or less (e.g., 1:3 or less, 1:4 or less, 1:5 or less, 1:6 or less, 1:7 or less, 1:8 or less, 1:9 or less, 1:10 or less, 1:12 or less, 1:15 or less, 1:20 or less, 1:25 or less, 1:30 or less, 1:35 or less, 1:40 or less, 1:45 or less, 1:50 or less, 1:60 or less, 1:70 or less, 1:80 or less, 1:90 or less, 1:100 or less, 1:125 or less, 1:150 or less, 1:175 or less, 1:200 or less, 1:250 or less, 1:300 or less, 1:350 or less, 1:400 or less, 1:450 or less, 1:500 or less, or 1:550 or less). In some embodiments, the acid equivalent weight ratio of (a) to (b) is from 1:600 to 1:6 (e.g., from 1:425 to 1:10, from 1:350 to 1:15, from 1:275 to 1:20, from 1:200 to 1:25, from 1:150 to 1:30, from 1:125 to 1:35, from 1:100 to 1:40, or from 1:80 to 1:50).

Formulations

The present disclosure also relates to formulations of the compositions and methods disclosed herein. In some embodiments, the formulation can be in the form of a single package formulation including both (a) aminopyralid or an agriculturally acceptable salt or ester thereof and (b) clopyralid or an agriculturally acceptable salt or ester thereof. In some embodiments, the formulation can be in the form of a single package formulation including both (a) and (b) and further including at least one additive. In some embodiments, the formulation can be in the form of a two-package formulation, wherein one package contains (a) and optionally at least one additive while the other package contains (b) and optionally at least one additive. In some embodiments of the two-package formulation, the formulation including (a) and optionally at least one additive and the formulation including (b) and optionally at least one additive are mixed before application and then applied simultaneously. In some embodiments, the mixing is performed as a tank mix (i.e., the formulations are mixed immediately before or upon dilution with water). In some embodiments, the formulation including (a) and the formulation including (b) are not mixed but are applied sequentially (in succession), for example, immediately or within 1 hour, within 2 hours, within 4 hours, within 8 hours, within 16 hours, within 24 hours, within 2 days, or within 3 days, of each other.

In some embodiments, the formulation of (a) and (b) is present in suspended, emulsified, or dissolved form. Exemplary formulations include, but are not limited to, aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, and materials for spreading or granules.

In some embodiments, (a) aminopyralid or an agriculturally acceptable salt or ester thereof and/or (b) clopyralid or an agriculturally acceptable salt or ester thereof is an aqueous solution that can be diluted before use. In some embodiments, (a) and/or (b) is provided as a high-strength formulation such as a concentrate. In some embodiments, the concentrate is stable and retains potency during storage and shipping. In some embodiments, the concentrate is a clear, homogeneous liquid that is stable at temperatures of 54° C. or greater. In some embodiments, the concentrate does not exhibit any precipitation of solids at temperatures of −10° C. or higher. In some embodiments, the concentrate does not exhibit separation, precipitation, or crystallization of any components at low temperatures. For example, the concentrate remains a clear solution at temperatures below 0° C. (e.g., below −5° C., below −10° C., below −15° C.). In some embodiments, the concentrate exhibits a viscosity of less than 50 centipoise (50 megapascals), even at temperatures as low as 5° C.

The compositions and methods disclosed herein can also be mixed with or applied with an additive. In some embodiments, the additive can be diluted in water or can be concentrated. In some embodiments, the additive is added sequentially. In some embodiments, the additive is added simultaneously. In some embodiments, the additive is premixed with the aminopyralid or agriculturally acceptable salt or ester thereof. In some embodiments, the additive is premixed with the clopyralid or agriculturally acceptable salt or ester thereof. In some embodiments, the additive is premixed with the aminopyralid or agriculturally acceptable salt or ester and the clopyralid or agriculturally acceptable salt or ester thereof.

In some embodiments, the additive is an additional pesticide. Exemplary additional pesticides include, but are not limited to, 2,4-D, aminocyclopyrachlor, acetochlor, aclonifen, amicarbazone, 4-aminopicolinic acid based herbicides, such as halauxifen, halauxifen-methyl, and those described in U.S. Pat. No. 7,314,849 (B2) and U.S. Pat. No. 7,432,227 (B2), amidosulfuron, aminopyralid, aminotriazole, ammonium thiocyanate, asulam, atrazine, beflubutamid, benazolin, bentazone, bifenox, bromacil, bromoxynil, butachlor, butafenacil, butralin, butroxydim, carbetamide, carfentrazone, carfentrazone-ethyl, chlormequat, chlorsulfuron, chlortoluron, cinidon-ethyl, clethodim, clodinafop-propargyl, clomazone, cyanazine, cyclosulfamuron, cycloxydim, dicamba, dichlobenil, dichlorprop-P, diclofop-methyl, diclosulam, diflufenican, diflufenzopyr, dimefuron, dimethachlor, diquat, diuron, EPTC, ET-751, ethoxysulfuron, fenoxaprop, fenoxaprop-ethyl, fenoxaprop-ethyl+isoxadifen-ethyl, fenoxaprop-P-ethyl, fenoxasulfone, flazasulfuron, florasulam, fluazifop, fluazifop-P-butyl, flucarbazone, flucarbazone-sodium, flucetosulfuron (LGC-42153), flufenacet, flumetsulam, flumioxazin, flupyrsulfuron, fluoroxypyr, fluoroxypyr-meptyl, flurtamone, glufosinate, glufosinate-ammonium, glyphosate, haloxyfop-methyl, haloxyfop-R, hexazinone, imazamethabenz, imazamox, imazapic, imazapyr, imazaquin, imazethapyr, imazosulfuron, indanofan, indaziflam, iodosulfuron, iodosulfuron-ethyl-sodium, ioxynil, isoproturon, isoxaben, isoxaflutole, lactofen, linuron, MCPA, MCPB, mecoprop-P, mesosulfuron, mesosulfuron-ethyl sodium, metazochlor, metosulam, metribuzin, metsulfuron, metsulfuron-methyl, MSMA, napropamide, norfurazon, orthosulfamuron, oryzalin, oxadiargyl, oxadiazon, oxyfluorfen, paraquat, pendimethalin, penoxsulam, picloram, picolinafen, pinoxaden, primisulfuron, profluazol, propaquizafop, propoxycarbazone, propyzamide, prosulfocarb, prosulfuron, pyraflufen-ethyl, pyrasulfotole, pyribenzoxim (LGC-40863), pyroxsulam, pyroxasulfone, quinmerac, quizalofop-ethyl-D, quizalofop-P-ethyl, quizalofop-P-tefuryl, rimsulfuron, sethoxydim, simazine, sulfentrazone, sulfometuron, sulfosate, sulfosulfuron, tebuthiuron, tepraloxydim, terbacil, terbutryn, thiazopyr, thifensulfuron, thifensulfuron-methyl, topramezone, tralkoxydim, triasulfuron, tribenuron, tribenuron-methyl, triafamone, triclopyr, and trifluralin, and agriculturally acceptable salts, esters and mixtures thereof. In some embodiments, the additional pesticide includes 2,4-D choline salt, triclopyr choline salt, aminocyclopyrachlor choline salt, or a mixture thereof.

In some embodiments, the compositions and methods disclosed herein do not incorporate naptalam (i.e., N-1-naphthylphthalamic acid or NPA) or the salts or esters thereof. In some embodiments, the compositions and methods disclosed herein are free of naptalam or the salts or esters thereof. In some embodiments, naptalam or the salts or esters thereof are not applied to the vegetation, the area adjacent to the vegetation, the soil, or the water, in the methods disclosed herein.

In some embodiments, the aminopyralid or an agriculturally acceptable salt or ester thereof is provided in a premixed formulation with an additional pesticide. In some embodiments, the aminopyralid or an agriculturally acceptable salt or ester thereof is premixed with clopyralid, fluoroxypyr, metsulfuron-methyl, 2,4-D, or mixtures thereof. Exemplary premixes of aminopyralid or an agriculturally acceptable salt or ester thereof and an additive that are or have been commercially available include, but are not limited to, SENDERO® (a premix incorporating clopyralid by Dow AGROSCIENCES LLC), CAPSTONE® (a premix incorporating triclopyr by Dow AGROSCIENCES LLC), CLEANWAVE0 (a premix incorporating fluoroxypyr by Dow AGROSCIENCES LLC), CHAPARRAL® and OPENSIGHT® (a premix incorporating metsulfuron-methyl by Dow AGROSCIENCES LLC), CLEARVIEW® (a premix incorporating metsulfuron-methyl by Dow AGROSCIENCES LLC), FOREFRONT® R&P and FOREFRONT® HL (a co-pack product incorporating 2,4-D by Dow AGROSCIENCES LLC), GRAZON-NEXT® and GRAZONNEXT® HL (a co-pack product incorporating 2,4-D by Dow AGROSCIENCES LLC), PASTUR-ALL® (a co-pack product incorporating 2,4-D by Dow AGROSCIENCES LLC), and RESTORE® (a co-pack product incorporating 2,4-D by Dow AGROSCIENCES LLC).

In some embodiments, the clopyralid or an agriculturally acceptable salt or ester thereof is provided in a premixed formulation with an additional pesticide. In some embodiments, the clopyralid or an agriculturally acceptable salt or ester thereof is premixed with acetochlor, benazolin, bensulfuron-methyl, 2,4-D, dicamba, flumetsulam, fluoroxypyr, glufosinate, glyphosate, imazamethabenz, imazamox, imazapic, imazapyr, imazaquin, imazethapyr, imazosulfuron, MCPA, triclopyr, or mixtures thereof. Exemplary premixes of clopyralid or an agriculturally acceptable salt or ester thereof and an additive that are or have been commercially available include, but are not limited to, CURTAIL® (a premix incorporating 2,4-D by Dow AGROSCIENCES LLC), MILLENIUM ULTRA 2® (a premix incorporating 2,4-D and dicamba by NUFARM AMERICAS INC.), SURESTART® (a premix incorporating acetochlor and flumetsulam by Dow AGROSCIENCES LLC), BENAZALOX® (a premix incorporating benazolin by BAYER CROPSCIENCE), KE CAOTE® (a premix incorporating bensulfuron-methyl by NANJING RED SUN CO., LTD.), HORNET® (a premix incorporating flumetsulam by Dow AGROSCIENCES LLC), WIDEMATCH® (a premix incorporating fluoroxypyr by Dow AGROSCIENCES LLC), HAT TRICK® (a premix incorporating fluoroxypyr and MCPA by LOVELAND PRODS., INC.), CURTAIL M® (a premix incorporating MCPA by Dow AGROSCIENCES LLC), CONFRONT® (a premix incorporating triclopyr by Dow AGROSCIENCES LLC), and REDEEM® (a premix incorporating triclopyr by Dow AGROSCIENCES LLC).

In some embodiments, the additive includes an agriculturally acceptable adjuvant. Exemplary agriculturally acceptable adjuvants include, but are not limited to, antifreeze agents, antifoam agents, compatibilizing agents, sequestering agents, neutralizing agents and buffers, corrosion inhibitors, colorants, odorants, penetration aids, wetting agents, spreading agents, dispersing agents, thickening agents, freeze point depressants, antimicrobial agents, crop oil, safeners, adhesives (for instance, for use in seed formulations), surfactants, protective colloids, emulsifiers, tackifiers, and mixtures thereof. Exemplary agriculturally acceptable adjuvants include, but are not limited to, crop oil concentrate (mineral oil (85%)+emulsifiers (15%)), nonylphenol ethoxylate, benzylcocoalkyldimethyl quaternary ammonium salt, blend of petroleum hydrocarbon, alkyl esters, organic acid, and anionic surfactant, $C_9$-$C_{11}$ alkylpolyglycoside, phosphate alcohol ethoxylate, natural primary alcohol ($C_{12}$-$C_{16}$) ethoxylate, di-sec-butylphenol EO-PO block copolymer, polysiloxane-methyl cap, nonylphenol ethoxylate+urea ammonium nitrate, emulsified methylated seed oil, tridecyl alcohol (synthetic) ethoxylate (8 EO), tallow amine ethoxylate (15 EO), and PEG (400) dioleate-99.

In some embodiments, the additive is a safener that is an organic compound leading to better crop plant compatibility when applied with a herbicide. In some embodiments, the safener itself is herbicidally active. In some, the safener acts as an antidote or antagonist in the crop plants and can reduce or prevent damage to the crop plants. Exemplary safeners include, but are not limited to, AD-67 (MON 4660), benoxacor, benthiocarb, brassinolide, cloquintocet (mexyl), cyometrinil, cyprosulfamide, daimuron, dichlormid, dicyclonon, dietholate, dimepiperate, disulfoton, fenchlorazole, fenchlorazole-ethyl, fenclorim, flurazole, fluxofenim, furilazole, harpin proteins, isoxadifen-ethyl, jiecaowan, jiecaoxi, mefenpyr, mefenpyr-diethyl, mephenate, naphthalic anhydride, 2,2,5-trimethyl-3-(dichloroacetyl)-1,3-oxazolidine, 4-(dichloroacetyl)-1-oxa-4-azaspiro[4.5]decane, oxabetrinil, 829148, and N-phenyl-sulfonylbenzoic acid amides, as well as agriculturally acceptable salts thereof and, provided they have a carboxyl group, their agriculturally acceptable derivatives. In some embodiments, the safener can be cloquintocet or an ester or salt thereof, such as cloquintocet (mexyl). For example, cloquintocet can be used to antagonize harmful effects of the compositions on rice and cereals.

Exemplary surfactants (e.g., wetting agents, tackifiers, dispersants, emulsifiers) include, but are not limited to, the alkali metal salts, alkaline earth metal salts and ammonium salts of aromatic sulfonic acids, for example lignosulfonic acids, phenolsulfonic acids, naphthalenesulfonic acids, and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenol ether, ethoxylated isooctyl-, octyl- or nonylphenol, alkylphenyl or tributylphenyl polyglycol ether, alkyl aryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g., methylcellulose), hydrophobically modified starches, polyvinyl alcohol, polycarboxylates, polyalkoxylates, polyvinyl amine, polyethyleneimine, polyvinylpyrrolidone and copolymers thereof.

Exemplary thickeners include, but are not limited to, polysaccharides, such as xanthan gum, and organic and inorganic sheet minerals, and mixtures thereof.

Exemplary antifoam agents include, but are not limited to, silicone emulsions, long-chain alcohols, fatty acids, salts of fatty acids, organofluorine compounds, and mixtures thereof.

Exemplary antimicrobial agents include, but are not limited to, bactericides based on dichlorophen and benzyl alcohol hemiformal, and isothiazolinone derivates, such as alkylisothiazolinones and benzisothiazolinones, and mixtures thereof.

Exemplary antifreeze agents, include, but are not limited to ethylene glycol, propylene glycol, urea, glycerol, and mixtures thereof.

Exemplary colorants include, but are not limited to, the dyes known under the names Rhodamin B, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, and mixtures thereof.

Exemplary adhesives include, but are not limited to, polyvinylpyrrolidone, polyvinyl acetate, polyvinyl alcohol, tylose, and mixtures thereof.

In some embodiments, the additive includes a carrier. In some embodiments, the additive includes a liquid or solid carrier. In some embodiments, the additive includes an organic or inorganic carrier. Exemplary liquid carriers include, but are not limited to, petroleum fractions or hydrocarbons such as mineral oil, aromatic solvents, paraffinic oils, and the like, vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like, esters of the above vegetable oils, esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, dibutyl adipate, di-octyl phthalate and the like, esters of mono, di and polycarboxylic acids and the like, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like, and water as well as mixtures thereof. Exemplary solid carriers include, but are not limited to, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, pyrophyllite clay, attapulgus clay, kieselguhr, calcium carbonate, bentonite clay, Fuller's earth, cottonseed hulls, wheat flour, soybean flour, pumice, wood flour, walnut shell flour, lignin, ammonium sulfate, ammonium phosphate, ammonium nitrate, ureas, cereal meal, tree bark meal, wood meal and nutshell meal, cellulose powders, and mixtures thereof.

In some embodiments, emulsions, pastes or oil dispersions can be prepared by homogenizing (a) and (b) in water by means of wetting agent, tackifier, dispersant or emulsifier. In some embodiments, concentrates suitable for dilution with water are prepared, comprising (a), (b), a wetting agent, a tackifier, and a dispersant or emulsifier.

In some embodiments, powders or materials for spreading and dusts can be prepared by mixing or concomitant grinding of (a) and (b) and optionally a safener with a solid carrier.

In some embodiments, granules (e.g. coated granules, impregnated granules and homogeneous granules) can be prepared by binding the (a) and (b) to solid carriers.

The formulations disclosed herein can comprise a synergistic, herbicidally effective amount of (a) and (b). In some embodiments, the concentrations of (a) and (b) in the formulations can be varied. In some embodiments, the formulations comprise from 1% to 95% (e.g., from 5% to 95%, from 10% to 80%, from 20% to 70%, from 30% to 50%) by total weight of (a) and (b). In some embodiments, (a) and (b), independently, can be employed in a purity of from 90% to 100% (e.g., from 95% to 100%) according to nuclear magnetic resonance (NMR) spectrometry. In some embodiments, the concentrations of (a), (b), and additional pesticides in the formulations can be varied. In some embodiments, the formulations comprise from 1% to 95% (e.g., from 5% to 95%, from 10% to 80%, from 20% to 70%, from 30% to 50%) by total weight of (a), (b), and additional pesticides. In some embodiments, (a), (b), and additional pesticides, independently, can be employed in a purity of from 90% to 100% (e.g., from 95% to 100%) according to NMR spectrometry.

Methods of Application

The compositions disclosed herein can be applied in any known technique for applying herbicides. Exemplary application techniques include, but are not limited to, spraying, atomizing, dusting, spreading, or direct application into water (in-water). The compositions can be applied directly (e.g., low volume foliar, high volume foliar, cut stump, basal, or soil concentration) or by broadcast applications. The method of application can vary depending on the intended purpose. In some embodiments, the method of application can be chosen to ensure the finest possible distribution of the compositions disclosed herein.

The compositions disclosed herein can be applied pre-emergence (before the emergence of undesirable vegetation) or post-emergence (i.e., during and/or after emergence of the undesirable vegetation). In some embodiments, the compositions disclosed herein are applied post-emergence when the undesirable vegetation starts with leaf development up to flowering. In some embodiments, the compositions disclosed herein are applied post-emergence to relatively immature undesirable vegetation to achieve the maximum control of weeds. In some embodiments when the compositions are used in crops, the compositions can be applied after seeding and before or after the emergence of the crop plants. In some embodiments, the compositions disclosed herein show good crop tolerance even when the crop has already emerged, and can be applied during or after the emergence of the crop plants. In some embodiments, when the compositions are used in crops, the compositions can be applied before seeding of the crop plants.

In some embodiments, the compositions disclosed herein are applied to vegetation or an area adjacent the vegetation or applying to soil or water to prevent the emergence or growth of vegetation by spraying (e.g., foliar spraying). For example, the composition can be applied aerially. In some embodiments, the spraying techniques use, for example, water as carrier and spray liquor rates of from 10 liters per hectare (L/ha) to 2000 L/ha (e.g., from 50 L/ha to 1000 L/ha, or from 100 to 500 L/ha). In some embodiments, the compositions disclosed herein are applied by the low-volume or the ultra-low-volume method, wherein the application is in the form of micro granules. In some embodiments, wherein the compositions disclosed herein are less well tolerated by certain crop plants, the compositions can be applied with the aid of the spray apparatus in such a way that they come into little contact, if any, with the leaves of the sensitive crop plants while reaching the leaves of undesirable vegetation that grows underneath or the bare soil (e.g., post-directed or lay-by).

In some embodiments, wherein the undesirable vegetation is treated post-emergence, the compositions disclosed herein are applied by foliar application. In some embodiments, herbicidal activity is exhibited by the compounds of the synergistic mixture when they are applied directly to the plant or to the locus of the plant at any stage of growth or before planting or emergence. The effect observed can depend upon the type of undesirable vegetation to be controlled, the stage of growth of the undesirable vegetation, the application parameters of dilution and spray drop size, the particle size of solid components, the environmental conditions at the time of use, the specific compound employed, the specific adjuvants and carriers employed, the soil type, and the like, as well as the amount of chemical applied. In some embodiments, these and other factors can be adjusted to promote non-selective or selective herbicidal action.

The compositions and methods disclosed herein can be used to control undesired vegetation in a variety of crop and non-crop applications. In some embodiments, the compositions and methods disclosed herein can be used for controlling undesired vegetation in crops. Exemplary crops include, but are not limited to, barley, canola (e.g., winter and spring oilseed rape), cereal, corn (maize), mint, mustard, rye, triticale, oats, spinach, sugar beet, turnips, wheat, pasture, rangelands, and cruciferous vegetables. In some embodiments, the compositions and methods disclosed herein can be used for controlling undesired vegetation in non-crop areas. Exemplary non-crop areas include, but are not limited to, turf, pasture, fallow, wildlife management areas, or rangeland. In some embodiments, the compositions and methods disclosed herein can be used in industrial vegetation management (IVM) or for utility, pipeline, roadside, and railroad rights-of-way applications. In some embodiments, the compositions and methods disclosed herein can also be used in forestry (e.g., for site preparation or for combating undesirable vegetation in plantation forests). In some embodiments, the compositions and methods disclosed herein can be used to control undesirable vegetation in conservation reserve program (CRP) lands, trees, vines, grasslands, and grasses grown for seeds. In some embodiments, the compositions and methods disclosed herein can be used on lawns (e.g., residential, industrial, and institutional), golf courses, parks, cemeteries, athletic fields, and sod farms.

The compositions and methods disclosed herein can also be used in crop plants that are resistant to, for instance, herbicides, pathogens, and/or insects. In some embodiments, the compositions and methods disclosed herein can be used in crop plants that are resistant to one or more herbicides because of genetic engineering or breeding. In some embodiments, the compositions and methods disclosed herein can be used in crop plants that are resistant to one or more pathogens such as plant pathogenous fungi owing to genetic engineering or breeding. In some embodiments, the compositions and methods disclosed herein can be used in crop plants that are resistant to attack by insects owing to genetic engineering or breeding. Exemplary resistant crops include, but are not limited to, corn (maize), sorghum, wheat, sunflower, rice, canola (oilseed rape), soybeans, cotton, alfalfa, clover, rye, barley, triticale, and sugarcane that are resistant to synthetic auxins, or crop plants that, owing to introduction of the gene for *Bacillus thuringiensis* (or Bt) toxin by genetic modification, are resistant to attack by certain insects. In some embodiments, the compositions and methods described herein also can be used in conjunction with glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil to control vegetation in crops tolerant to glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, bromoxynil, or combinations thereof. In some embodiments, the undesirable vegetation is controlled in glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil tolerant crops possessing multiple or stacked traits conferring tolerance to multiple chemistries and/or multiple modes of action. In some embodiments, the undesired vegetation is controlled in phenoxy acid tolerant crops and the phenoxy acid tolerant crops have tolerance conferred by an AAD12 gene. The combination of (a), (b), and a complementary herbicide or salt or ester thereof can be used in combination with herbicides that are selective for the crop being treated and which complement the spectrum of weeds controlled by these compounds at the application rate employed.

The herbicidal compositions prepared disclosed herein are effective against a variety of types of undesirable vegetation. In some embodiments, the compositions disclosed herein can be used for controlling broadleaf weeds. Exemplary broadleaf weeds include, but are not limited to, *Polygonum* species such as wild buckwheat (*Polygonum convolvolus*), *Amaranthus* species such as pigweed (*Amaranthus retroflexus*), *Chenopodium* species such as common lambsquarters (*Chenopodium album* L.), *Sida* species such as prickly *sida* (*Sida spinosa* L.), *Ambrosia* species such as common ragweed (*Ambrosia artemisiifolia*), *Acanthospermum* species, *Anthemis* species, *Atriplex* species, *Cirsium* species, *Convolvulus* species, *Conyza* species, such as horseweed (*Conyza canadensis*), *Cassia* species, *Commelina* species, *Datura* species, *Euphorbia* species, *Geranium* species, *Galinsoga* species, *Ipomoea* species (morning-glory), *Lamium* species, *Malva* species, *Matricaria* species, *Prosopis* species, *Rumex* species, *Sysimbrium* species, *Solanum* species, *Trifolium* species, *Xanthium* species, *Veronica* species, *Viola* species, common chickweed (*Stella ria media*), velvetleaf (*Abutilon theophrasti*), Hemp sesbania (*Sesbania exaltata* Cory), *Anoda cristata* (spurred anoda), *Bidens pilosa* (common blackjack), *Brassica kaber* (wild mustard), *Capsella bursa pastoris* (Shepherd's purse), *Centaurea cyanus* (cornflower), *Galeopsis tetrahit* (common hempnettle), *Galium aparine* (cleavers), *Helianthus annuus, Desmodium tortuosum* (tall tick-clover), *Kochia scoparia* (Kochia), *Medicago Arabica* (spotted medick), *Mercurialis annua* (annual mercury), *Myosotis arvensis* (field forget-me-not), *Papaver rhoeas* (common poppy), *Raphanus raphanistrum* (jointed charlock), *Salsola kali* (prickley saltwort), *Sinapis arvensis* (wild mustard), *Sonchus arvensis* (field sowthistle), *Thlaspi arvense* (field pennycress), *Tagetes minuta* (tall khakiweed), *Richardia brasiliensis* (Brazil callalily), *Plantago major* (rat's-tail plantain), and *Plantago lanceolata* (narrow-leaved plantain). In some embodiments, the undesirable vegetation includes a species of the *Solanaceae* family. In some embodiments, the undesirable vegetation includes black nightshade (*Solanum nigram*).

By way of non-limiting illustration, examples of certain embodiments of the present disclosure are given below.

Examples

Evaluation of Aminopyralid Potassium Salt and Clopyralid-Olamine for Post-Emergence Synergistic Weed Control Field trials were conducted with applications made to established grassland with naturally occurring weed populations. The target plants were treated with postemergence foliar applications when they reached three to five inches tall. All treatments were applied using a randomized complete block trial design, with 4 replications per treatment.

Treatments consisted of aminopyralid potassium salt and clopyralid-olamine, each in water and applied alone or in combination. When the aminopyralid potassium salt or clopyralid-olamine were applied individually, the treatment also included applying 0.5 liters per hectare (L/ha) of ACTIROB® (available from BAYER CROPSCIENCE) to the plant material. When the aminopyralid potassium salt or clopyralid-olamine were applied together, the treatment also included applying 1 L/ha (1 g ae/ha) of ACTIROB® (available from BAYER CROPSCIENCE) to the plant material. Spray solutions were prepared using an appropriate amount of dilution to form a 2-liter (L) aqueous spray solution with active ingredients in single and two way combinations. Formulated compounds were applied to the plant material with a backpack sprayer equipped with 8003 nozzles calibrated to deliver 187 L/ha at a spray height of 18 inches (43 centimeters (cm)) above average plant canopy. The treated plants were black nightshade (*Solanam nigram*). The treated plots and control plots were rated blind at various intervals after application. Ratings were based on a scale of 0-100%, as discussed above, wherein 0% indicates no damage to the undesired vegetation and 100% indicates complete destruction of the undesired vegetation.

Colby's equation was used to determine the herbicidal effects expected from the mixtures, as described above. The results were measured at 56 days after the first application of the compositions. The trials exhibited unexpected synergy, and those results were found statistically significant under the p-value test. The herbicide tank-mix combination tested, application rates employed, plant species tested, and results are given below.

nents, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method of controlling undesirable vegetation, which comprises applying to vegetation or an area adjacent the vegetation or applying to soil or water to control the emergence or growth of vegetation a composition comprising (a) aminopyralid, or an agriculturally acceptable salt or ester thereof and (b) clopyralid, or an agriculturally acceptable salt or ester thereof,

| Weed Bayer | Evaluation Interval | Aminopyralid Potassium Salt | | Clopyralid-olamine | | Combination | |
|---|---|---|---|---|---|---|---|
| | | g ae/ha | Mean % weed control | g ae/ha | Mean % weed control | Measured mean % weed control | Colby predicted mean % weed control |
| SOLNI | 56 days | 1 | 0 | 90 | 37.5 | 60 | 37.5 |

As shown above, the samples demonstrated synergistic weed control, with higher measured weed control than would be predicted by the Colby equation.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, compowherein the undesirable vegetation comprises a species from the Solanaceae family;

wherein (a) and (b) are each added in an amount sufficient to produce a synergistic herbicidal effect;

wherein (a) and (b) are applied in an acid equivalent weight ratio of (a) to (b) of from 1:100 to 1:60, wherein (a) is applied in an amount of from 0.1 to 10 g ae/ha, and wherein the composition does not contain an additional pesticide.

2. The method of claim 1, wherein the undesirable vegetation is controlled in barley, canola, cereal, corn, mint, mustard seed, oats, spinach, sugar beet, turnips, or wheat.

3. The method of claim 1, wherein acid equivalent weight ratio of (a) to (b) is from 1:100 to 1:80.

4. The method of claim 1, wherein the acid equivalent weight ratio of (a) to (b) is 1:90.

* * * * *